United States Patent [19]
Tuli

[11] Patent Number: 5,818,956
[45] Date of Patent: Oct. 6, 1998

[54] EXTENDED FINGERPRINT READING APPARATUS

[76] Inventor: Raja Singh Tuli, 55 City Centre Dr. Suite 500, Mississauga, Ontario, Canada, L5B 1M3

[21] Appl. No.: 546,787

[22] Filed: Oct. 23, 1995

[51] Int. Cl.⁶ .................................................. G06K 9/00
[52] U.S. Cl. ...................... 382/126; 356/71; 340/825.34
[58] Field of Search .................................. 382/124, 125, 382/126, 127; 356/71; 250/206.1; 340/825.34; 348/161

[56] References Cited

U.S. PATENT DOCUMENTS

| | | | |
|---|---|---|---|
| 4,120,585 | 10/1978 | DePalma et al. | 356/71 |
| 4,340,300 | 7/1982 | Ruell | 356/71 |
| 4,537,484 | 8/1985 | Fowler et al. | 382/126 |
| 4,553,837 | 11/1985 | Marcus | 356/71 |
| 4,613,987 | 9/1986 | Keverian | 382/321 |
| 4,684,802 | 8/1987 | Hakenwerth et al. | 356/71 |
| 4,783,167 | 11/1988 | Schiller et al. | 382/126 |
| 5,177,802 | 1/1993 | Fujimoto et al. | 382/124 |
| 5,448,649 | 9/1995 | Chen et al. | 382/126 |

FOREIGN PATENT DOCUMENTS

| | | |
|---|---|---|
| 3424955 | 1/1986 | Germany . |
| 1180685 | 7/1989 | Japan . |
| 2146691 | 6/1990 | Japan . |
| 492990 | 3/1992 | Japan . |

*Primary Examiner*—Christopher S. Kelley

[57] ABSTRACT

The present invention is a miniature fingerprint reading device capable of extracting and accurately reproducing the ridge orientations on the skin of a fingertip. The illumination, focusing and reading elements follow the finger's curvature to provide a much larger surface area fingerprint comparable to conventional inking methods. The present invention virtually eliminates the occurrence of skewed images as there are restrictions to the angle at which any finger is read. Trapezoidal distortion is also eliminated as the fingerprint image is always at a fixed distance from the reading elements.

4 Claims, 4 Drawing Sheets

EXTENDED FINGERPRINT READING APPARATUS

BACKGROUND OF THE INVENTION

The present invention relates to an apparatus and a method for producing a fingerprint ridge extraction system to accurately reproduce fingerprint images, revealing a larger print area than conventional reading devices which position the finger on a planar transparent platen. The heart of the invention lies in the implementation of a reading technique utilizing an array of image sensor elements, which read the ridge orientation when uniformly illuminated, whereby the reading and illumination components of the apparatus follow the curvature of the finger to better define ridge patterns on the skin around a fingertip. The functionality of the device is quite unique as it simply involves placing the user's finger on a curved surface or flexible membrane, applying a constant pressure on the device for proper imaging, with the reading and illumination sources traversing in a similar curved path to remain focused. This provides a simple economical construction with no complicated mechanisms and few moving parts yielding a reliable device.

The main application for the present invention and devices of the art is in identification or security purposes, as fingerprints remain consistent throughout life and no two are alike. A particularly useful application of the device is in conjunction with pattern recognition software means, to identify similarities between fingerprints being scanned and those already scanned and stored on computer systems. Fingerprinting is an established and reliable method of personal identification, and is useful as the basis for a pattern recognition security access system.

Prior art in this field would involve fingerprint reading devices whereby the user places a finger on a fixed planar glass platen, below which a lens system focuses the illuminated ridge pattern onto a two dimensional area CCD (Charged Coupled Device) chip. Other art which may use optical sensor elements to replace a CCD do not utilize a curved surface or flexible membrane to increase the surface area of the scanned portion of the finger.

The main problem associated with most prior art systems for this particular application is the limited surface area of a fingerprint extracted by applying pressure of the finger onto a planar surface. Such electronic reading devices do not produce similar printed areas as conventional inking methods which capture the sides of a finger, and may contain important identification marks for recognition purposes. Hence, the present invention proves to be useful in providing larger electronic images of conventional sizes. Furthermore, other embodiments involve placing the finger in a circular or elliptical tube and rotating it past the reading elements, whereby the finger applies the correct force required for reading, opposed to stationary platen type devices of prior art.

Other advantages associated with the present invention over prior art planar fingerprint reading devices, include the reduced occurrence of skewed images which present a major problem to pattern recognition software, as the angle at which the finger is placed on the platen can vary significantly. The present invention virtually eliminates the occurrence of skewed images as there are restrictions to the angle at which any finger is read. Trapezoidal distortion is also eliminated as the fingerprint image is always at a fixed distance from the reading elements, unlike prior art devices which use a prism from which this problem arises.

SUMMARY OF THE INVENTION

In a principle aspect of the present invention, a compact fingerprint reading device capable of extracting and accurately reproducing the ridge pattern on the skin of a fingertip following the fingers curvature, is provided.

In a further aspect of the present invention, the fingertip to be read is placed in contact with a curved transparent surface, whereby the fingerprint area to be read is in continuous contact with this curved surface which provides more contact area than a planar surface, enabling a much larger fingerprint area to be read.

In a further aspect of the present invention, the curved transparent surface also acts as a guide rail or reference to which the reading, focusing, and illumination elements traverse, as these elements must maintain a fixed distance from the curved surface whilst traversing all areas of the fingerprint to be read.

In a second embodiment of the present invention, the fingerprint to be read is placed on a thin flexible transparent membrane which is elastic in nature and deforms to the contours of each fingers profile as it is depressed on the membrane.

In this second embodiment of the present invention, the flexible membrane's deformed profile also acts as a guide rail or reference to which the reading, focusing, and illumination elements traverse, as these elements must maintain a fixed distance from the curved surface whilst traversing all areas of the fingerprint to be read.

In a third embodiment of the present invention, the fingerprint is obtained by placing the finger inside a transparent circular or elliptical tube mounted to the housing of the device, whereby the transparent tube is rotated by the finger as the ridge orientations are extracted with the aid of reading, focusing, and illumination elements, which remain stationary in the housing at a fixed distance from the finger.

In a further aspect of all embodiments of the present invention, a patterned strip is placed against the curved transparent surfaces or membranes, which is read simultaneously with the fingerprint, whereby the dark and light strips indicate to the device's microprocessor when a single line of the fingerprint has been read, controlling the rate at which information is read.

BRIEF DESCRIPTION OF DRAWINGS

This invention maybe better understood and its numerous objects and advantages will become apparent to those skilled in the art by reference to the accompanying drawings as follows.

DETAILED DESCRIPTION OF PREFERRED EMBODIMENTS

Figure 1A:
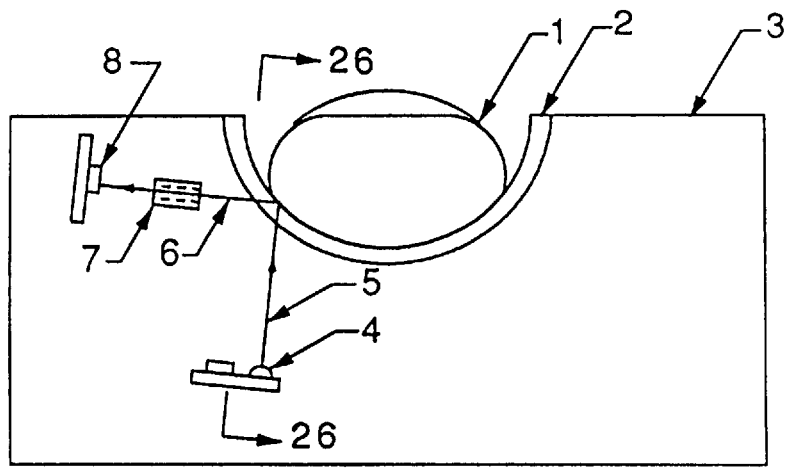
FIG. 1a illustrates the elements of the fingerprint reading device commencing a reading operation under a curved transparent surface onto which the finger is placed, in accordance with a first embodiment of the present invention.
Figure 1B:
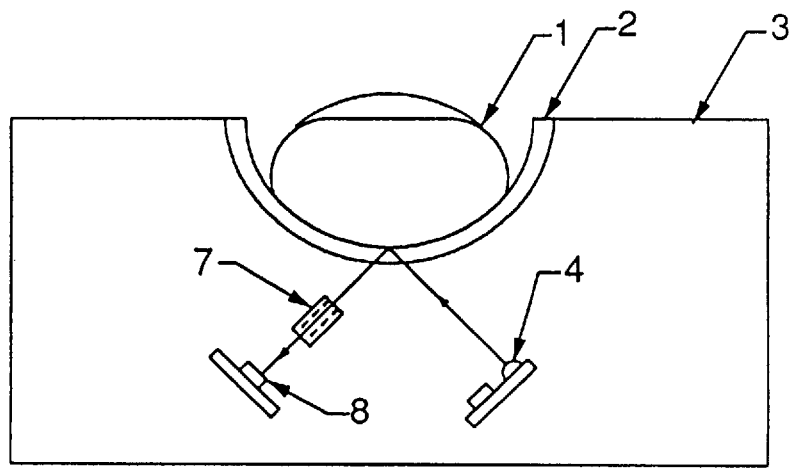
FIG. 1b illustrates the elements of the fingerprint reading device during the reading operation under a curved transparent surface onto which the finger is placed, in accordance with a first embodiment of the present invention.

For a better understanding of the invention, reference is first made to FIG. 1a which represents the layout of elements within a first embodiment of the invention, in an initial position prior to reading a fingerprint. The finger 1 is placed inside a curved transparent surface 2 of uniform thickness, which generally follows the curvature of most fingers, providing a larger surface area contact than any planar surface yielding a larger fingerprint. The curved transparent surface 2 is mounted to a housing 3 within which the reading elements are contained. An illumination source 4 comprised of an array of illumination elements, directs a beam of light 5 towards the finger 1 and is reflected of the ridge orientations, with varying intensities containing information essential to the reconstruction of the fingerprint. The beam 5 extends beyond the width of the fingerprint, and the reflected rays 6 are focused by a Selfoc optic fibre lens array 7, onto a linear array of reading elements 8 comprised of optical sensor integrated circuits. In a secondary embodiment of this particular embodiment, the Selfoc optic fibre lens array 7 can be replaced by a camera type lens, and the reading elements 8 can be a CCD, to perform the same reading function using alternate technology. The various intensities of the reflected rays 6 produce proportional outputs from the optical sensors 8 representing the ridge and valley locations on the fingerprint, creating a digital representation of each line of the fingerprint. The device's microprocessor circuitry determines the cutoff voltage levels, whereby valleys are distinguished from ridges based on the magnitude of the outputs from the optical sensors 8. Using a cutoff voltage produces a black and white representation of the fingerprint, whereas alternate means which do not use cutoff voltages produce grey scale fingerprints. The curved transparent surface 2 also acts as a reference or guide rail for the reading elements 8, lens array 7, and illumination source 4, which remain fixed relative to each other as they traverse in a path about the curved surface 2, equidistant to it at all points of travel keeping the fingerprint image always in focus. The fingerprint is read in lines, whereby each line is read and sent to a memory buffer after which the reading elements, lens array, and illumination source are advanced to the location of the next line of the fingerprint to perform the same function. Approximately half way through the reading operation, the reading elements 8, lens array 7, and illumination source 4 are shown in their identical relative locations but focused on a different position of the finger, equidistant from the curved transparent surface 2, as illustrated in FIG. 1b. Upon completing a reading operation:, the reading elements 8, lens array 7, and illumination source 4 assume the position illustrated in FIG. 1c, on the opposite side of the finger from the initial position always equidistant from the curved transparent surface 2.

Figure 2:
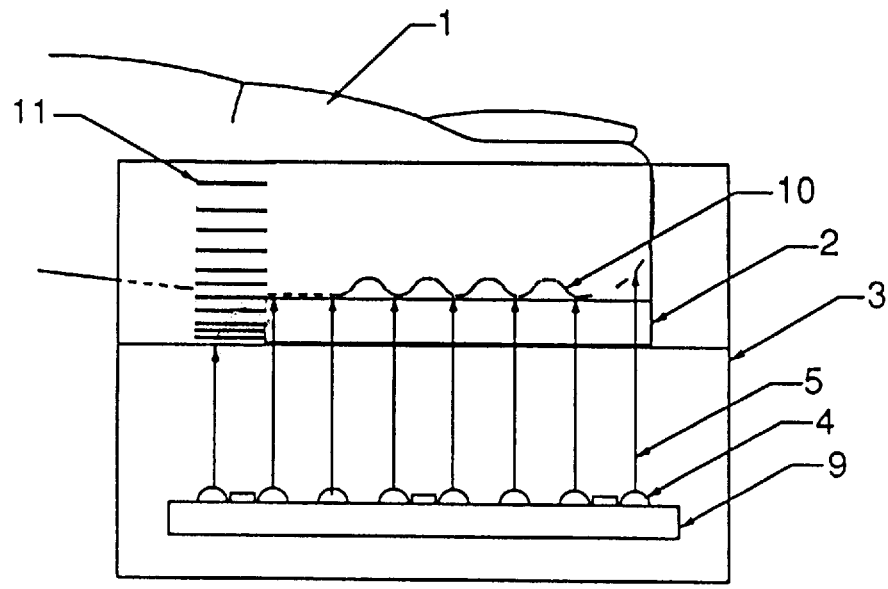
FIG. 2 represents the sectional view 26–26 of FIG. 1a, in accordance with a first embodiment of the present invention.

For a better understanding of the device in accordance with the first embodiment of the invention, a sectional view 'A—A' across FIG. 1a is illustrated in FIG. 2. A linear array of illumination elements 4 are mounted to a circuit board 9 within the housing 3, to direct a beam of light 5 towards the ridge orientations 10 of the finger 1, which is then reflected to the reading elements. The curved transparent surface 2 positions the finger accurately within the housing, for reading together with a patterned strip 11 affixed to this surface controlling the rate of reading each line of the fingerprint. The beam of light 5 extends the full width of the ridge orientations 10 and also extends to the patterned strip 11.

Figure 1C:
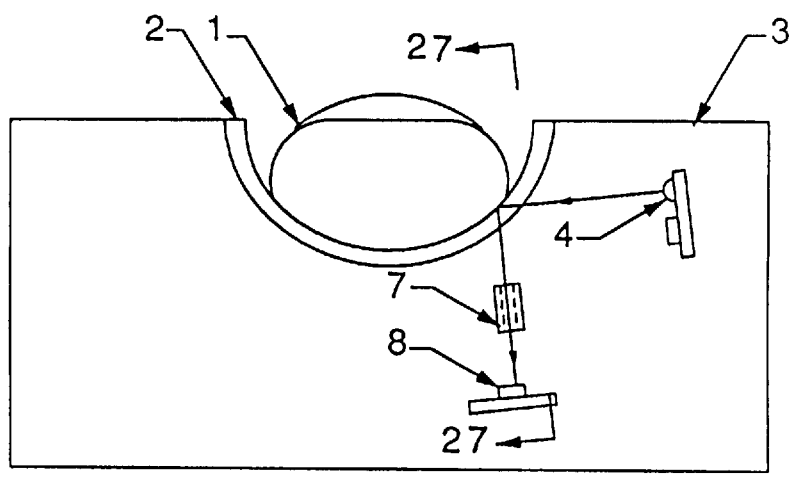
FIG. 1c illustrates the elements of the fingerprint reading device upon completing the reading operation under a curved transparent surface onto which the finger is placed, in accordance with a first embodiment of the present invention.
Figure 3:
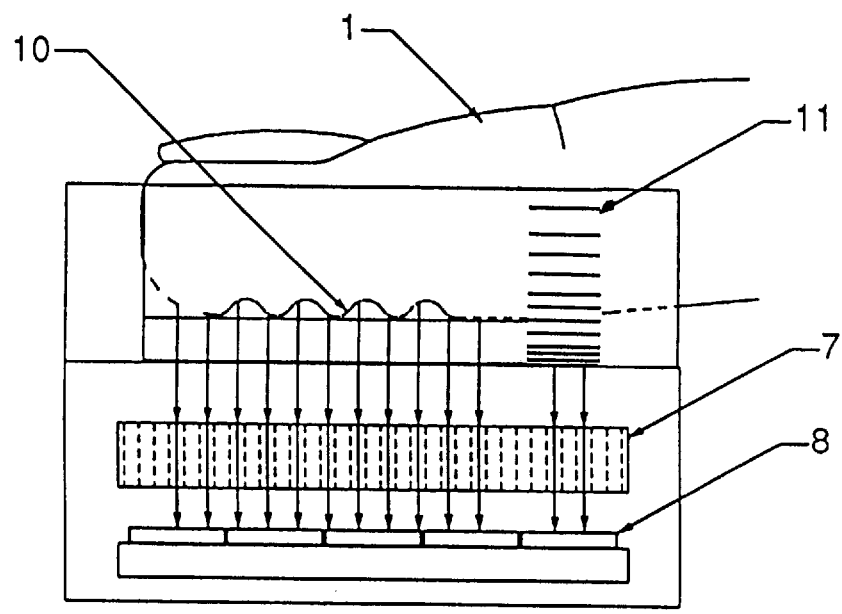
FIG. 3 represents the sectional view 27—27 of FIG. 1c, in accordance with a first embodiment of the present invention.

Reference is now made to FIG. 3 which represents a sectional view 'B–B' across FIG. 1c to better explain the fingerprint reading device, in accordance with the first embodiment. As rays of light contact the ridge orientations 10 of a finger 1 and also the patterned strip 11, they are reflected and focused through a lens array 7 onto optical sensor integrated circuits 8, which produce an electrical output representing a digital image of the fingerprint.

Figure 4:
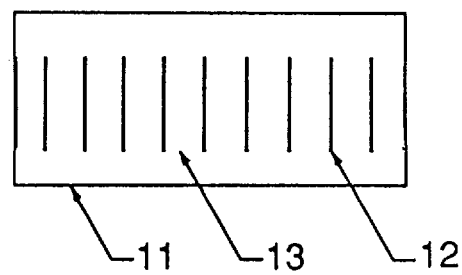
FIG. 4 illustrates a patterned strip placed against the curved transparent surfaces or membranes to control the information reading rate, in accordance with all embodiments of the present invention.

To further understand the method for controlling reading at a fixed rate, reference is made to FIG. 4 which illustrates the patterned strip 11 of FIGS. 2 & 3 shown in a flat layout as the reading elements detect it from the curved path traversed. The patterned strip 11 is comprised of dark elements 12 and light elements 13 in an alternate sequence of arrangement, whereby those dark and light elements are detected by the reading elements. Individual lines of the fingerprint are read by reading elements simultaneously with the pattern of strip 11, which align the fingerprint image to this pattern. As the device's microprocessor senses a dark or light element of strip 11, each line is read by the reading elements and transferred to a memory buffer, then the reading elements are advanced to the next line aligned to an opposite shade in strip 11. Upon detecting a new shade in strip 11 corresponding to a new fingerprint line, the reading process is repeated and the reading elements advanced to the next line. In other embodiments where the finger moves relative to the reading elements fixed within the housing, the strip 11 moves together with the finger and is critical in determining the rate of reading and in particular, exactly when the individual lines of the fingerprint are sent to the memory buffer, as each line is read many times per second but sent to the memory buffer only when a different shade in strip 11 is encountered by the reading elements. Individual lines of the fingerprint are also read by reading elements simultaneously with the pattern of strip 11, which align the fingerprint image to this pattern.

Figure 5A:
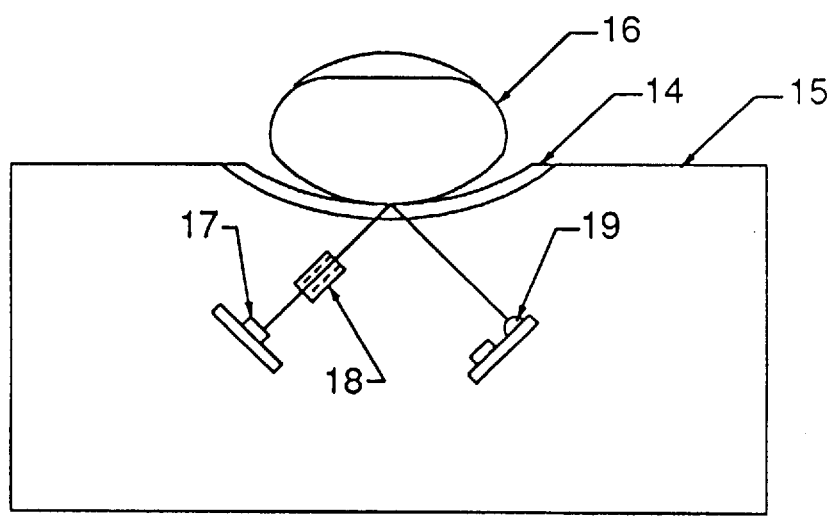
FIG. 5a represents a thin flexible elastic transparent membrane onto which the finger is placed, at its rest position prior to following the curvature of any finger, in accordance with a second embodiment of the present invention.
Figure 5B:
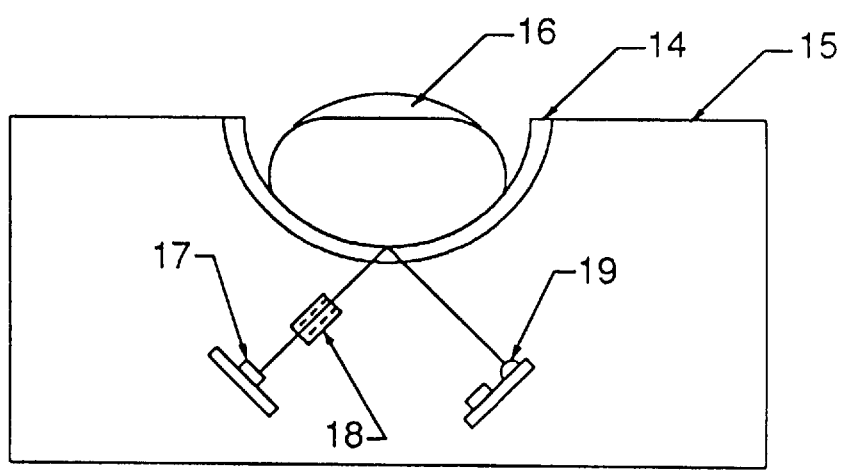
FIG. 5b represents a thin flexible elastic transparent membrane onto which the finger is placed at its fully deformed position, following the finger's curvature including its sides, in accordance with a second embodiment of the present invention.

In a second embodiment of the present invention, a transparent flexible elastic membrane 14 of uniform thickness affixed to the housing 15, is used as a means to follow the curvature of a finger 16. FIG. 5a illustrates this flexible membrane in a rest position prior to following the finger's curvature. In this position, the surface area contacted is minimal and increases significantly as the flexible membrane 14 is depressed to the position of FIG. 5b, whereby the reading elements 17, Selfoc optic fibre lens array 18, and illumination source 19 are fixed relative to each other as they traverse in a path which follows the shape of the transparent flexible membrane 14, in the position of FIG. 5b, equidistant to it at all points of travel to maintain a constant focal distance. The purpose of using a flexible membrane is to adapt to various finger profiles as there is considerable variation in size and curvature, resulting in a larger contacted surface area than planar surfaces or fixed curved surfaces. The fingerprint is read in lines, whereby each line is read and sent to a memory buffer after which the reading elements, lens array, and illumination source are advanced to the location of the next line of the fingerprint to perform the same function. The method for controlling the reading rate is as previously explained with the aid of FIG. 4, utilizing the patterned strip 11 affixed to the transparent flexible membrane 14.

Figure 6A:
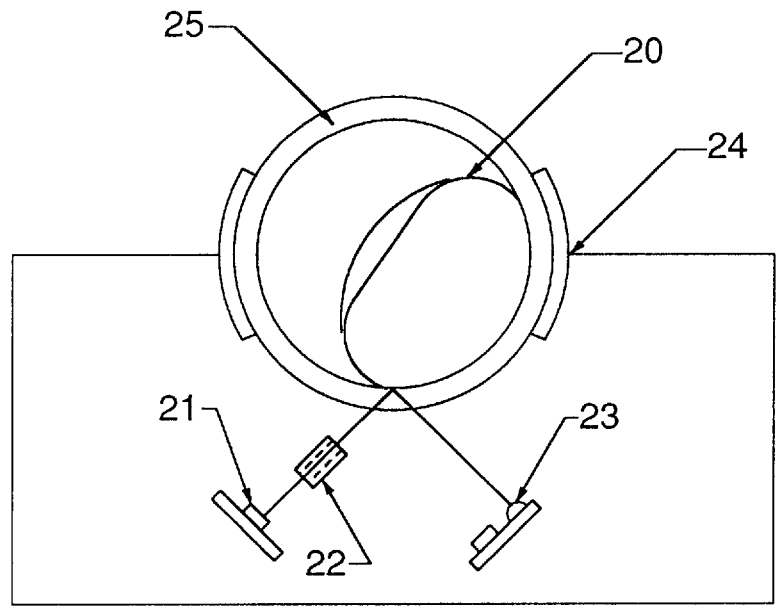
FIG. 6a illustrates the finger inside a transparent circular or elliptical tube mounted to rotate in the housing of the device, commencing a reading operation, in accordance with a third embodiment of the present invention.
Figure 6B:
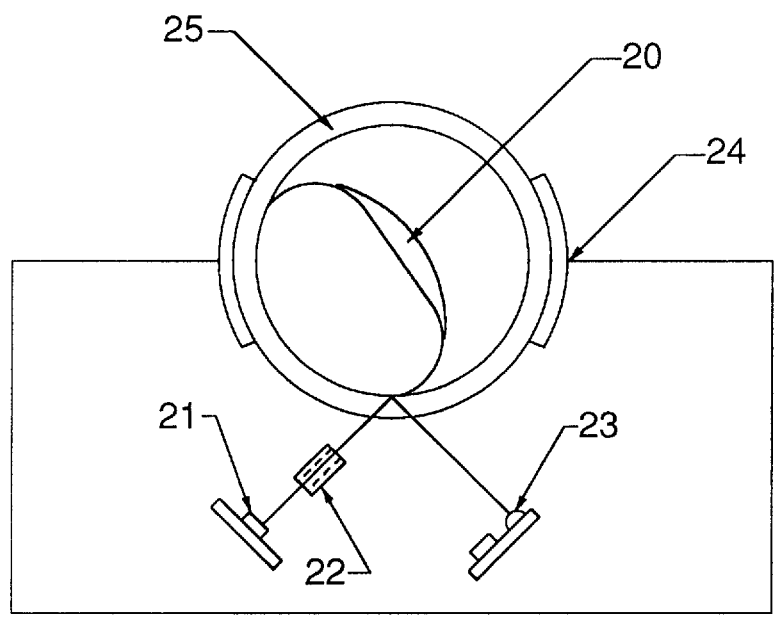
FIG. 6b illustrates the finger inside a transparent circular or elliptical tube mounted to rotate in the housing of the device, upon completing the reading operation, in accordance with a third embodiment of the present invention.

In a third embodiment of the present invention, a rotary fingerprint reading device is constructed in accordance with FIG. 6a, which illustrates the finger 20 in an initial reading position. In this particular embodiment, the reading elements 21, Selfoc optic fibre lens array 22, and illumination source 23 are attached to the housing 24, and the finger is rotated past these fixed elements. The finger 20 is placed inside a transparent circular or elliptical tube 25 of uniform thickness, which is mounted and rotates in the housing 24 of the device, with the surface area contacted always at a constant distance from the lens array 22 for precise focusing of the ridge orientations on the fingertip. In the initial reading position of FIG. 6a, the finger 20 is positioned to allow reading to commence from one side at the extreme point of contact with the transparent circular or elliptical tube 25. Upon rotating the circular or elliptical tube 25 due to the applied force of the finger, producing sufficient friction without slipping against the contacted surface area, the finger reaches a terminal position of FIG. 6b with an electronic mapping of the fingerprint obtained by the reading elements. The method for controlling the reading rate is as previously explained with the aid of FIG. 4, utilizing the patterned strip 11 affixed to the transparent circular or elliptical tube 25, and read simultaneously with the fingerprint.

It is also understood that the following claims are intended to cover all of the general and specific features of the invention herein described, and all statements of the scope of the invention which, as a matter of language, might be said to fall therebetween.

I claim:

1. A fingerprint reading device comprising:

a transparent flexible membrane of uniform thickness which when depressed follows the profile of a finger, making full contact with the fingerprint area including the sides of the finger;

said transparent flexible membrane fixed to a housing inside which an illumination source, a Selfoc optic fibre lens array, and a linear array of reading elements remain fixed relative to each other, traversing in a path identical to the curvature of the transparent membrane from one side of the finger to the other where contact is made, equidistant to the transparent flexible membrane throughout the path traversed;

said reading elements which read one line of the fingerprint at a time, whereby each line is parallel to the long axis of the finger, advancing to consecutive lines upon completing the reading operation for each line;

said illumination source which directs a linear beam of light to the fingerprint, is focused by a Selfoc lens array on the reading elements to produce outputs proportional to the intensity of incident light for each picture element, creating a digital representation of each line.

2. A fingerprint reading device comprising:

a transparent circular or elliptical tube of uniform thickness which follows the profile of a finger when inserted inside said tube, making full contact with the fingerprint area including the sides of the finger;

said transparent circular or elliptical tube rotating within a housing inside which an illumination source, a Selfoc optic fiber lens array, and a linear array of reading elements remain fixed within the housing, with the finger rotating past the reading elements due to the applied force of the finger, producing sufficient friction without slipping against the contacted surface area, such that the transparent circular tube remains at a fixed distance from the Selfoc optic fiber lens array throughout its rotation;

said reading elements which read one line of the fingerprint at a time, whereby each line is parallel to the long axis of the finger, reading consecutive lines as the finger is rotated;

said illumination source which directs a linear beam of light to the fingerprint, is focused by a Selfoc lens array on the reading elements to produce outputs proportional to the intensity of incident light for each picture element, creating a digital representation of each line;

whereby a patterned strip of alternate dark and light elements on the transparent surface upon which the finger rests, is read by optical sensor elements which align the fingerprint image to this pattern.

3. A fingerprint reading device as claimed in claim 1 whereby a patterned strip of alternate dark and light elements on the transparent surface upon which the finger rests, is read by optical sensor elements which align the fingerprint image to this pattern.

4. A fingerprint reading device as claimed in claim 1 whereby the reading elements are comprised of a Charged Coupled Device, and the focusing means is comprised of an optic lens system.

* * * * *